US006794153B2

(12) United States Patent
Yi et al.

(10) Patent No.: US 6,794,153 B2
(45) Date of Patent: Sep. 21, 2004

(54) HELICOBACTER PYLORI ANTIGENS IN BLOOD

(75) Inventors: Ching Sui A. Yi, Burlingame, CA (US); Chung-Ho Hung, Burlingame, CA (US)

(73) Assignee: Panion & BF Laboratory Ltd., Taipei (TW)

( * ) Notice: Subject to any disclaimer, the term of this patent is extended or adjusted under 35 U.S.C. 154(b) by 0 days.

(21) Appl. No.: 10/041,510

(22) Filed: Jan. 10, 2002

(65) Prior Publication Data

US 2002/0090660 A1 Jul. 11, 2002

Related U.S. Application Data

(63) Continuation-in-part of application No. 09/572,598, filed on May 17, 2000, now abandoned.
(60) Provisional application No. 60/170,537, filed on Dec. 14, 1999.

(51) Int. Cl.[7] ............................................. G01N 33/554
(52) U.S. Cl. ......................... 435/7.32; 435/7.1; 435/7.2; 435/7.35; 435/7.37; 435/7.92; 435/7.93; 435/7.94; 435/975; 436/518; 436/526; 436/806; 436/824; 424/184.1
(58) Field of Search ........................ 435/7.1, 7.2, 7.32, 435/7.35, 7.37, 7.92, 7.93, 7.94, 975, 252.3, 69.1, 69.6, 69.7, 8, 12, 252.1, 961, 960, 66, 7.21; 436/518, 526, 806, 824, 66; 424/184.1

(56) References Cited

U.S. PATENT DOCUMENTS

| | | | | |
|---|---|---|---|---|
| 4,034,074 | A | * | 7/1977 | Miles ............................. 424/1 |
| 4,145,406 | A | * | 3/1979 | Schick et al. .................. 424/1 |
| 4,271,140 | A | * | 6/1981 | Bunting ......................... 424/1 |
| 4,459,359 | A | * | 7/1984 | Neurath ....................... 436/507 |
| 5,384,240 | A | * | 1/1995 | Hyman et al. ................ 435/5 |
| 5,716,791 | A | | 2/1998 | Larka et al. |
| 5,837,472 | A | * | 11/1998 | Labigne ....................... 435/7.1 |
| 5,871,942 | A | | 2/1999 | Larka et al. |
| 5,932,430 | A | | 8/1999 | Larka et al. |
| 6,051,416 | A | * | 4/2000 | Pace et al. ................. 435/252.1 |
| 6,153,390 | A | * | 11/2000 | Cover et al. ................... 435/6 |
| 6,348,318 | B1 | * | 2/2002 | Valkirs ....................... 435/7.1 |
| 6,638,752 | B2 | * | 10/2003 | Contag .................... 435/252.3 |

FOREIGN PATENT DOCUMENTS

| | | | |
|---|---|---|---|
| EP | 0 329 570 | 8/1989 | ......... G01N/33/569 |
| EP | 0 806 667 | 11/1997 | ......... G01N/33/569 |
| WO | 97/03359 | * 1/1997 | ......... G01N/33/569 |
| WO | 98/43479 | * 10/1998 | ........... A01N/43/04 |
| WO | 99/41611 | 8/1999 | ......... G01N/33/569 |
| WO | 00/29432 | 5/2000 | ......... C07K/14/195 |

OTHER PUBLICATIONS

Kostrzynska, M et al, Journal of Bacteriology, Feb. 1991, vol. 173(3), pp. 937–946.*
Chmiela, M et al, Immunology Letters, Apr. 1998, vol. 61(2–3), pp. 119–115, Anti–Lewis X antibody and Lewis S–anti–LewisX immune complexes in Helicobacter pylori infection.*
Cook, PJ et al, OJM–Monthly Journal of the Asscoiation of Physicians, 1996, vol. 89(10), Oct., pp. 727–735, Infectious agents and atherosclerotic vascular disease.*
Fleisch, F et al, Clinical infectious diseases, Feb. 1998, vol. 26(2), pp. 526–527, Helicobacter species strain Mainz isolated from cultures of blood from two patients with AIDS.*
Hsueh, PR et al, Journal of clinical microbiology, Jun. 1999, vol. 37(6), pp. 2084–2086, Septic shock due to Helicobacter fennelliae in a non–HIV infected heterosexual patient.*
Hung, CC et al, Journal of Formosan Medical Association, 1997, vol. 96(7), pp. 558–560, Bacteremia casued by Helicobacter pylori cinaedi in an AIDS patient.*
Husmann, M et al, Journal of Clinical Microbiology, vol. 32(12), pp. 3037–3039, Dec. 1994, Helicobacter sp. Strain Mainz isolated from an AIDS patient with septic arthritis: Case Report and Nonradioactive analysis of 16S rRNA sequence.*
Kemper, C.A e tal, Journal of Infection, vol. 26, 1993, pp. 97–101, Helicobacter (Campylobacter ) fennelliae–like organisms an an important but occult cause of bacteraemia in a patient with AIDS.*
Kiehlbauch, JA etal, Annals of internal medicine, Jul. 15, 1994, vol. 121(2), pp. 90–93, Helicobacter cinaedi–associated bacteremia and cellulitis in immunocompromised patients.*
Lastovica, AJ et al, Abstracts of the General Meeting of the American Society for Microbiology, vol. 97(0), p. 168, May 4–8, 1997, Campylobacter/Helicobacter bacteraemia in South African paediatric patinets.*
Lastovica, AJ, Campylobacters Helicobacters and related Organisms, 1995, 8ty ,pp. 475–480, Campylobacter/Helicobacter bacteraemia in Cape Town, South Africa 1997–1995.*
Lee et al, Gut, vol. 41(suppl. 1), p. A76, 1997, Does blood in the stomach influence the diagnosis of H.pylori infection in patients with bleeding peptic ulcer?*
Nagata, H et al, Feb. 1999, Microbial Pathogenesis, vol. 26, 103–110, Application of Bead–ELISA method to detect Helicobacter pylori VacA.*

(List continued on next page.)

*Primary Examiner*—Lynette R. F. Smith
*Assistant Examiner*—Ginny Allen Portner
(74) *Attorney, Agent, or Firm*—Fei-Fei Chao; Venable LLP

(57) ABSTRACT

The present invention relates to the finding and detection of *Helicobacter pylori* (*H. pylori*) antigens in blood of infected individuals. The *H. pylori* antigens are components of *H. pylori* cells which include, but not limited to DNA, RNA, and fragments of nucleotides, proteins or peptides. *H. pylori* DNA, RNA, and fragments of nucleotides can be detected by polymerase chain reaction (PCR), ligase chain reaction (LCR), or DNA hybridization methods or other amplification methods. *H. pylori* proteins or peptides or other antigenic components thereof can be detected by immunoassays or immunoblot using an antibody against *H. pylori*, preferably an antibody purified by an affinity column. The present invention further provides immunoassay methods, diagnostic kits, and an immunochromatographic assay device for detection of *Helicobacter pylori* antigens in serum samples.

25 Claims, No Drawings-

OTHER PUBLICATIONS

Ndawula, EM et al, European journal of clinical microbiology & infectious diseases, Jul. 1994, vol. 13(7), p. 621, *Helicobacter pylori* bacteraemia [letter].*

Reinauer, S et al, Schonlein–Henoch purpura associated with gastric *Helicobacter pylori* infection, Journal of the American Academy of Dermatology, Nov. 1995, vol. 33(5 pt 2), pp. 876–879.*

Sullivan, AK et al, International journal of STD & AIDS, Jan. 1997, Voo. 8(1), pp. 59–60, Recurrent *Helicobacter cinaedi* cellulitis and bacteraemia in a patient with HIV infection.*

Tee, W et al, Scandinavian journal of infectious diseases, 1996, vol. 28(2), pp. 199–203, *Helicobacter cinaedi* bacteraemia: varied clinical manifestations in three homosexual males.*

Trivett–Moore, NL et al, Jouranl of clinical microbiology, May 1997, vol. 35(5), pp. 1144–1150, *Helicobacter westmeadii* sp. nov., a new specieas isolated from blood cultures of two AIDS patients.*

Weir, SC et al, Journal of clinical microbiology, Aug. 1999, vol. 37(8), pp. 27–29–2733, An uncommon Helicobacter isolate from blood:evidence of a grouup of Helicobacter spp. pathogenic in AIDS patients.*

Amano, K et al, Clinical and Diagnostic Laboratory Immunology, vol. 4(5), pp. 540–544, Sep. 1997, Reactivities of Lewis Antigen Monoclonal antibodies with the Lipopolysaccharides of *Helicobacter pylori* strains isolated from patients with gastroduod.*

Marshall, Barry; *Helicobacter pylori*—The Etiologic Agent for Peptic Ulcer; JAMA, Oct. 4, 1995, vol. 274, No. 13, p 1064–1066.

Howden, Colin; Testing for *H. pylori* in the Post–treatment Period; The American Journal of Medicine, May 20, 1996, vol. 100 (suppl 5A), p. 5A–39S–5A–41S.

Cutler, Alan; Testing for *Helicobacter pylori* in Clinical Practice; The American Journal of Medicine, May 20, 1996, vol. 100 (suppl 5A), p. 5A–35–5A–38S.

Genta, Robert; Simultaneous Visualization of *Helicobacter pylori* and Gastric Morphology: a New Stain; Human Pathology, Mar. 1994, vol. 25, No. 3, p. 221–226.

Ham, S.W.: Transport and Storage of *Helicobacter pylori* from Gastric Mucosal Biopsies and Clinical Isolates; Eur. J. Clin. Microbiol. Infect. Dis., vol. 14, 1995, p. 349–352.

Jang–Jih Lu et al.: "Comparison of five PCR methods for detection of *Helicobacter pylori* DNA in gastric tissues" Journal of Clinical Microbiology, vol. 37, No. 3, Mar. 1999, pp. 772–774, XP002163333.

* cited by examiner

HELICOBACTER PYLORI ANTIGENS IN BLOOD

RELATED APPLICATION

The present application is a continuation-in-part (CIP) application which claims the priority of U.S. Provisional patent application Ser. No. 60/170,537, filed on Dec. 14, 1999, and U.S. Utility patent application Ser. No. 09/572,598, filed on May 17, 2000 now abandoned, which are herein incorporated by reference.

FIELD OF THE INVENTION

The present invention relates to the finding of *Helicobacter pylori* (*H. pylori*) antigens and antigenic fragments thereof in blood, which includes whole blood, plasma, and serum. The *H. pylori* antigens found in blood include, but not limited to, *H. pylori* DNA, RNA, or fragments thereof, or *H. pylori* proteins/peptides or other antigenic components thereof. *H. pylori* DNA or fragments thereof are detected by polymerase chain reaction (PCR), ligase chain reaction (LCR), DNA hybridization, branched DNA signal amplification assay, or other signal amplification methods. *H. pylori* RNA thereof are detected by PCR, hybridization or other signal amplification assays. *H. pylori* proteins or peptides or other antigenic components thereof are detected by immunoassays or immunoblotting using an affinity purified antibody against *H. pylori*. The present invention also relates to diagnosing *H. pylori* infection by detecting the *H. pylori* antigens in blood.

BACKGROUND OF THE INVENTION

*Helicobacter pylori* (*H. pylori*) is a gram-negative bacterium which infects the gastric mucosal and is responsible for most peptic ulcer disease (PUD). Until recently, ulcers and other forms of dyspepsia were thought to be related to stress levels or eating habits. Recently, the medical community has confirmed that *H. pylori* is the causative agent for certain forms of gastric distress, including ulcers and gastric cancer. Eradication of *H. pylori* promotes healing of ulcer and greatly reduces the incidences of cancer and PUD.

*H. pylori* causes most gastric and duodenal ulcers, as well as peptic ulcer disease (PUD). The linkage of *H. pylori* and PUD was first discovered and published by Australian physicians Warren and Marshall in 1984 (*Lancet* I: 1311–1344). The *H. pylori* infection is now accepted as the most common cause of gastritis, and is etiologically involved in gastric ulcer, duodenal ulcer, gastric adenocarcinoma and primary B-cell lymphoma.

It has been proven that PUD is curable and rather easily. The cause of most PUD is infection with *H. pylori*. However, *H. pylori* infection is not routinely diagnosed, possibly because methods of testing for *H. pylori* infection are not satisfactory to physicians, especially the primary care physicians (i.e. invasive biopsy test). Therefore, primary physicians have tended to treat symptomatic patients with antisecretory agents.

Physicians need a simple, accurate and inexpensive diagnostic test for *H. pylori* infection so that they know when to treat patients and when to refer the patients to a gastroenterologist. However, the currently available *H. pylori* tests, which can be categorized as invasive tests and noninvasive tests, are not completely satisfactory.

The invasive tests require the use of endoscope followed by biopsy procedure. The tissue samples taken by the biopsy procedure can then be analyzed by culture, histology, or rapid urease testing.

Although culturing of the biopsy specimens provides the most reliable results for *H. pylori* testing, the reports of successful rates in a good laboratory are only between 70% and 80% (Han, S. W., et al., *Eur. J. Clin. Microbiol. Infect. Dis.* (1995), 14:349–352). Histological examination of special stained biopsy specimens can provide the direct evidence of acute or chronic inflammatory mucosal cells and lesions. However, it requires the collaborations of both an endoscopist and a pathologist (Genta, R. M., et al., *Hum. Pathol.* (1994), 25:221–226). Rapid urease tests detect the rise in pH from ammonia produced by *H. pylori* urease, which splits urea into ammonia and carbon dioxide. However, it requires a high density of bacteria and anything that reduces the bacterial load may produce a false-negative (Cutler, A. F., *Am. J. Med.* (1996), 100:35S–39S).

A number of noninvasive tests have been developed to detect the presence of *H. pylori* infection since 1990. For example, the Urea Breath Testing is based on the urease activity of the organism, which splits urea labeled with $^{13}C$ or $^{14}C$ into nonradioactive $^{13}CO_2$ or radioactive $^{14}CO_2$. The urea breath test is widely recommended for confirming eradication of *H. pylori* 4 weeks after therapy.

U.S. Pat. Nos. 5,716,791, 5,871,942, and 5,932,430 disclose immunoassays for detecting *H. pylori* antigens in stool specimens using a polyclonal antibody which is obtained from sensitizing animal with *H. pylori* cells (i.e., ATCC strain 43504). The antibody is purified by DEAE (diethylaminoethyl cellulose) column. Although the stool antigen test is reported to be satisfactory, the collection and process of the stool specimens are found to be difficult and unpleasant. Many patients are unwilling to provide stool samples to physician due to offensive odor and lack convenient collection device.

Serologic testing of serum *H. pylori* antibodies using ELISA is another widely used test. Examples of the latter techniques can be found in a U.S. Pat. No. 5,262,156 and EP Pat. No. 0 329 570. There have been several major antigens identified and used in immunoassays in the detection of *H. pylori* antibodies. However, these assays have not exhibited the specificity and sensitivity that are desired in serodiagnosis. (Newell, D. G., et al., *Serodian. Immunother. Infec. Dis.*, (1989), 3:1–6). One of the problems derives from cross-reactivity. That is because the dominant antigens in *H. pylori* (e.g., the putative flagellar protein which has a molecular weight of 60 Da) are not specific to *H. pylori*. Some of these antigens can be found in other bacteria such as *C. jeuni* and *C. coli*. A second problem that has been encountered in designing immunoassays for *H. pylori* is strain variation. Substantial differences in the antigens have been observed in different strains of *H. pylori*. These problems preclude designing an assay around the use of a single antigen. One approach that has been taken to improving the specificity and selectivity of antibody immunoassays for *H. pylori* has been to use a mixture of antigens from different *H. pylori* strains which mixture is enriched with certain antigen fragments. One ELISA which detects *H. pylori* antibodies in blood sera is commercially available. This assay uses a bacterial whole cell lysate as the antigen.

There are other disadvantages of using an ELISA which employs antigens to detect the presence of *H. pylori* antibodies in serum. In particular, the antibody titer in human sera remains high for a prolonged time (in some cases as much as twelve months) after the infection has been treated. Consequently, a positive test using this ELISA does not necessarily mean that the patient is currently infected and requires treatment for *H. pylori* infection. When confronted with a positive ELISA, treating physicians often order a gastric biopsy to confirm the presence of the bacteria before initiating antibiotic therapy. Therefore, the antigen-based ELISA does not eliminate the need for the invasive procedure.

It is therefore the object of the present invention to design a noninvasive and highly accurate diagnostic test for *H. pylori* infection. During the course of the investigation, *H. pylori* antigens in blood are discovered, which are in the forms of DNA or fragments thereof, or proteins/peptides or other antigenic components thereof, exist in blood, including whole blood, plasma and serum. Special methods for detecting these *H. pylori* antigens are thus designed to provide evidence that antigenic fragments of *H. pylori* are existed in blood. These methods include, but not limited to, polymerase chain reaction (PCR), ligase chain reaction (LCR) and DNA hybridization for detecting nucleic acid fragments of *H. pylori*, using primers or oligonucleotides specific for *H. pylori* and/or DNA probes derived from *H. pylori* strains. Additionally, immunoassays and immunoblotting are also developed for detecting protein/peptide or any antigenic components of *H. pylori*, using an affinity purified antibody against *H. pylori*.

As of this time, there has been no report with regard to the existence of *H. pylori* antigens in blood. The present invention will be the first to prove that *H. pylori* antigens not only exist in blood, but can be detected by the methods presented in the following sections.

SUMMARY OF THE INVENTION

The present invention provides *H. pylori* antigens which are existed in patient's blood and can be detected by polymerase chain reaction (PCR), ligase chain reaction (LCR), DNA hybridization, RNA hybridization, branched DNA assay, immunoblotting, and immunoassay. The present invention also provides methods for diagnosing *H. pylori* infection by detecting the *H. pylori* antigens in blood.

The term "antigens" used in the present invention broadly covers any substances which are directly or indirectly capable, under appropriate conditions, of inducing a specific immune response and of reacting with the products of the response, that is, with specific antibody or specifically sensitized T-lymphocytes, or both. Examples of these substances include, but are not limited to, proteins/peptides, polysaccharides, lipids, and poly- or oligo-nucleotides.

There are particularly two special kinds of *H. pylori* antigens that can be detected in blood. The first kind relates to polynucleotides or oligonucleotides which are chromosomal DNA, RNA or fragments thereof from *H. pylori*. This kind of *H. pylori* can be detected by polymerase chain reaction (PCR), ligase chain reaction (LCR), and hybridization (preferably spotted DNA hybridization) methods or other amplification methods.

The PCR method provided in the present invention requires the use of a pair of primers specific for detecting *H. pylori*. The term "primer" as used herein refers to an oligonucleotide, whether occurring naturally or produced synthetically, which is capable of acting as a point of initiation of nucleic acid synthesis when placed under conditions in which synthesis of a primer product which is complementary to a nucleic acid strand is induced, i.e., in the presence of four different nucleotide triphosphates with appropriate enzymes at a suitable temperature. The term "oligonucleotide" as used herein is defined as a molecule comprised of two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning.

The primers are prepared based upon conserved sequence found in consensus fragments of *H. pylori* strains, such as ATCC strains 43504, 43571, 43629, and 49053. The preferred primers range is from 15 to 25 base pairs (bps), most favorably about 20 bps in length. Better amplification can be obtained when both primers (forward and reverse primers) are the same length and with roughly the same nucleotide composition. The preferred blood sample for PCR is plasma.

The LCR method provided in the present invention requires the use of a DNA ligase and two sets of oligonucleotides which are specific to *H. pylori*. The preferred DNA ligase is Pfu DNA ligase, which is a thermostable DNA ligase isolated from *Pyrococcus furiosus* and is commercially available. The two sets of oligonucleotides for LCR is preferably longer in length than the primers for PCR. Like the PCR primers, the LCR oligonucleotides are derived from conserved sequence of the consensus fragments of *H. pylori* strains, such as ATCC strains 43504, 43571, 43629, and 49053.

LCR is performed by repeated cycles of heat denaturation of a DNA template containing a target sequence, annealing a first set of two adjacent oligonucleotide probes to the target DNA sequence in a unique manner, and a second set of complementary oligonucleotide probes that hybridize to the sequence opposite to the target DNA sequence. The term "target sequence" used herein refers to the "chromosomal DNA or fragments thereof" found in blood samples. Thereafter, the DNA ligase can covalently link each pair of adjacent probes provided there is complete complementary at the junction of the two adjacent probes.

The hybridization method requires the preparation of an *H. pylori* DNA probe. The *H. pylori* DNA probe is prepared by cutting out and extracting DNA fragment from *H. pylori* nucleic acid extracts after agarose gel electrophoresis. The probe normally has at least about 25 bases, more usually at least about 30 bases, and may have up to about 10,000 bases or more, usually having not more than about 5,000 bases. This DNA fragment is then digested with restriction endonucleases and ligated with a vector to form a recombinant plasmid construct, which can transfect eucaryotic or procaryotic host cells. The DNA fragment can be propagated in the host cells and re-isolated. The propagated DNA fragment can then be labeled with radioisotope (such as $^{32}P$, $^{3}H$, $^{14}C$, or the like) or fluorescence (such as the use of digoxigenin- and biotin-labeled DNA probes coupled with fluorescence detection methods) and used as a DNA probe.

The hybridization method is carried out by treating the nucleic acid sample from blood, preferably serum, with a denaturation agent to denature DNA on a solid phase support such as a nitrocellulose filter. The preferred denaturation agent include, but not limited to, alkali solution, elevated temperatures, organic reagents (e.g., alcohols, amides, amines, ureas, phenols and sulfoxides), or certain inorganic ions (e.g., thiocyanate and perchlorate). The labeled DNA probe will then be added to the denatured DNA spotted filter. The filter may then be assayed for the presence of DNA hybrids in the nature of the label. If the label is radioactive, the filter can be exposed to X-ray film. If the label is fluorescence, the filter can be viewed directly using a fluorescence microscope.

The second kind of antigens relates to *H. pylori* proteins and/or peptides, or any substances containing antigenic epitopes in blood which can be detected by immunoblotting or immunoassay, preferably using an affinity purified antibody against H. pylori antigens. Both primary and secondary antibodies may be required for detecting or measuring H. pylori antigens in blood, depending upon the kinds of methods used in the detection. A primary antibody is an antibody raised against an antigen, which in this case is the H. pylori antigen. The secondary antibody is an antibody against the immunoglobulin of a primary antibody producing species (such as goat anti-rabbit IgG). The preferred blood sample for the detection is serum.

Immunoblotting method is carried out by first analyzing blood sample with SDS-PAGE. After electrophoresis, the proteins/peptides bands are transferred to a nitrocellulose filter, which is then incubated with sufficient amount of anti-H. pylori antibody. An enzyme conjugated secondary antibody against the immunoglobulin of the animal species producing the anti-H. pylori can be added to the nitrocellulose filter. One of the preferred enzyme for this method is alkaline phosphatase, wherein the reaction can be detected by adding 5-bromo-4-chloro-3-indolylphosphate. Another preferred enzyme marker used in this method is horseradish peroxidase, which can be detected by adding 4-chloro-1-naphthol, tetramethylbenzidine, or 3,3'-diaminobenzidine to produce colored insoluble product for visualization.

The immunoassay methods comprise, but not limited to, basic sandwich assay, triple sandwich assay, and immunochromatographic assay.

In the basic sandwich assay, two primary antibodies are required, in which one is bound to a solid carrier and the other is labeled with a detection agent. The triple sandwich assay requires the combined use of two primary antibodies (namely, the first antibody and the second antibody) against H. pylori, in which only one primary antibody is required to be bound to a solid carrier, and one secondary antibody against the immunoglobulin of the animal species producing the unbounded primary antibody to form a complex against the antibody-antigen-antibody complex. The secondary antibody is labeled with a detection agent.

The solid carrier for the sandwich assays can be plastic beads, polyethylene, polystyrene, polypropylene, etc. The detection agent can be an enzymatic marker (such as alkaline phosphatase or horseradish peroxidase), a fluorescent or luminescent agent (such as fluorescein, rhodamine, or europium, luminol, or acridium), a radioisotope labeling (such as $I^{125}$), or a color particle (such as gold, silver, blue-latex, or selenium).

Both the basic and triple sandwich immunoassays require the interaction of a first primary antibody against H. pylori to form an antigen-antibody complex, followed by contacting the antigen-antibody complex with a second antibody against H. pylori.

The immunochromatographic assay also requires the combined use of the two primary antibodies against H. pylori. Contrasting to the basic and triple sandwich assays, the first antibody (i.e., the antibody which is in touch with the biological specimen first) is labeled with color particles. The second antibody is bound to a solid carrier such as nitrocellulose (or nitrocellulose derivative) membrane, nylon membrane, polyester membrane, filter paper, agarose or sephedex gel. The preferred solid carrier for the immunochromatographic assay is the nitrocellulose membrane. Optionally, a secondary antibody against the animal species for producing the first antibody can be added and/or bound to the solid carrier at near the end of the chromatographic strip opposite to the sample addition site. This secondary antibody is used as a control for capturing the unbound color particles at the end of the chromatographic run. Thus, if the sample does not contain H. pylori antigens, the color particles labeled first antibody will run through the second antibody without binding to it because no antibody-antigen-antibody complex is formed. However, because the secondary antibody is against the immunoglobulin of the first antibody producing animal, it will bind to the first antibody when it runs by regardless whether the first antibody has form a complex with the sample. The binding between the first antibody and the secondary antibody shows the end of the immunochromatographic run.

One of the problems in dealing with serum sample is that a patient infected with H. pylori often carries with him/her H. pylori antibodies in the serum. These serum H. pylori antibodies can form immune complexes with serum H. pylori antigens which may have impact on the accuracy of the immunoassays of the present invention. The ways to dissociate the H. pylori immune complexes include, but not limited to, dissociating the complexes with a dissociation reagent or at a sample dissociation condition.

Examples of the dissociation reagent include, but not limited to, high salts (e.g., 0.2 M to 1.5 M of 1 M NaCl, or KCl (most preferably, 1 M of NaCl or KCl), detergents (e.g., 0.1 to 2.0% (most preferably 1%) of sodium dodecyl sulphate (SDS), 0.1 to 2.0% (most preferably 1%) of TWEEN 20, 0.1 to 2.0% (most preferably 1%) of octylglucoside, 0.1 to 2.0% (most preferably 1%) of deoxycholate, or 0.1 to 2.0% (most preferably 1%) of TRITON X-100), chaotropic agents (e.g., 0.5 M to 6 M of guanidine HCl, 0.5 M to 8 M of urea, or 0.5 M to 3 M of KSCN), organic solvents (e.g., 10% dioxane or 40% ethylene glycol), enzymes (e.g., 1 to 10 units/ml of proteases (such as trypsin, chymotrypsin, pepsin, V8 protease, and subtilisin) or 1 to 10 units/ml of lipases (such as lipoprotein lipase from bovine milk, and lipase from *Candida rugosa*)). After the completion of the dissociation, the dissociation reagent can be removed from the serum samples by conventional methods such as dilution, filtration, column chromatography, or dialysis.

Examples of sample dissociation condition include, but not limited to, high pH (e.g., pH $\geq 9$) or low pH (e.g., pH $\leq 3$), and/or elevated temperature (e.g., at least 50° C.). After the completion of the dissociation, the condition of the serum sample can be re-adjusted back to the original pH (i e., at pH 7.4) or temperature (i e., at room temperature) by conventional methods.

Furthermore, the dissociation treated serum sample can be treated with a protein based reagent to minimize cross-reactivity. The preferred protein based reagent contains at least one of the following proteins: fetal bovine serum, pig serum, normal goat serum, horse serum, casein, albumin, gelatin, and bovine serum albumin.

DETAILED DESCRIPTION OF THE INVENTION

Although numerous attempts have been reported which provide quantitative and qualitative measurements for H. pylori infection in patients, none is directed to the testing of H. pylori in blood samples. The major reason is because no investigators has ever assumed that H. Pylori antigens could be found in the blood stream.

However, in the tables (i.e., Tables 1–3) to be presented within Examples 9 (Table 1) and 11 (Tables 2 and 3), infra, evidence will show that H. pylori antigens can be and have been found in serum samples of patients with H. pylori infection.

Based upon these findings, it is the object of the present invention to utilize the detectable H. pylori antigens in blood as tools for diagnosing H. pylori infection. The diagnostic methods which can be used to detect different kinds of H. pylori antigens which include, but not limited to, polymerase chain reaction (PCR), ligase chain reaction (LCR), branched DNA amplification assay, hybridization assay, immunoblot, immunoprecipitation, flow cytometry, immunoelectrophoresis, and immunoassays (e.g., enzyme-linked immunosorbent assay [ELISA], radioimmunoassay [RIA], and immunochromatography).

PCR is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Each of the DNA sequences can be separated by agarose gel electrophoresis followed by nucleic acid sequencing. The preferred type of blood sample for PCR is plasma. That is because the heme molecules from the hemoglobin contained within red blood cells may interfere with PCR amplification if hemolysis occurs.

The ligase chain reaction (LCR) is a DNA amplification technique which can be used to detect trace levels of known nucleic acid sequences. LCR involves a cyclic two-step reaction: (1) A high-temperature melting step in which double stranded target DNA unwinds to become single-stranded, and (2) a cooling step in which two sets of adjacent, complementary oligonucleotides anneal to the single-stranded target molecules and ligate together with DNA ligase. The products of the ligation from one cycle serve as templates for the next cycle's ligation reaction. LCR results in the exponential amplification of the ligation products in a manner analogous to the exponential amplification of template in the PCR reaction.

Both PCR and LCR require the findings of H. pylori specific primers or oligonucleotides to initiate the nucleic acids chain reaction. Because H. pylori strains are highly diverse at a genetic level (Fujimoto et al., J. Clin. Microbiol., (1994), 32:331–334) and individuals can be infected with more than one strain, it is therefore instrumental to design the primers or oligonucleotides based upon the conserved sequence of consensus fragments found in various strains of H. pylori.

H. pylori cells from ATCC strain 43504 have been found to be particularly useful for producing primary antibody against H. pylori in stool samples (See U.S. Pat. No. 5,716,791). That is because the antibodies produced through sensitization using cells from strain 43504 can detect the organism across geographic regions and dietary groups. Other H. pylori strains, such as ATCC 43571, 43629, 49053, have demonstrated similar antigenic capability. Therefore, it is worthwhile to find consensus fragments among these strains. This can be performed by digesting the extracted nucleic acids from the above mentioned H. pylori strains with the same restriction endonuclease(s), followed by running the digested H. pylori nucleic acid fragments through an agarose gel electrophoresis. The consensus fragments can be cut out and extracted. The nucleotide sequences of the consensus fragments can be analyzed. The conserved sequence of the consensus fragments can then be used for designing the primers or oligonucleotides for PCR or LCR.

In addition to PCR or LCR, the presence of H. pylori antigens in a blood sample may be detected using nucleic acid hybridization probes. The preferred nucleic acid hybridization probe is no more than about 5,000 bases. The probe sequence is preferably at least substantially complementary to the nucleotide sequence of a consensus fragment among H. pylori strains. In addition to the consensus fragment found in various H. pylori strains, the probe may be obtained from messenger RNA, from cDNA obtained by reverse transcription of messenger RNA with reverse transcriptase or by cleavage of the genome. After isolation and characterization of the desired probe, the DNA fragment of the probe may be cloned and propagated in host cells. The propagated probe can then be labeled with an atom or inorganic radical, most commonly using radionuclides, but also perhaps heavy metals or fluorescence. It may be feasible to employ an antibody which may bind specifically to the probe hybridized to the single stranded DNA of the H. pylori antigen. In this instance, the antibody would be labeled to allow for detection. The same types of labels which are used for the probe may also be bound to the antibody in accordance with known techniques.

A radioactive label such as $^{32}P$, $^{3}H$, $^{14}C$, or the like may be employed in labeling the probe, although other radioactive labels can also be used as long as they provide for an adequate signal having sufficient half-life. Other labels include ligands, which can serve as a specific binding member to a labeled antibody fluorescers, chemiluminescers, enzymes, antibodies which can serve as a specific binding pair member for a labeled ligand, and the like. A wide variety of labels used in immunoassays can also be used. The choice of the label is governed by the effect of the label on the rate of hybridization and binding of the probe to the sample DNA. It is necessary that the label provide sufficient sensitivity to detect the amount of DNA available for hybridization. Other considerations include the ease of synthesis of the probe, readily available instrumentation, ability to automate, convenience, and the like.

The manner in which the label is bound to the probe varies depending upon the nature of the label. For a radioactive label, a wide variety of techniques can be employed. Commonly employed is nick translation with an $\alpha$-$^{32}P$-dNTP or terminal phosphate hydrolysis with alkaline phosphatase followed by labeling with radioactive $^{32}P$ employing $\gamma$-$^{32}P$-NTP and T4 polynucleotide kinase. Alternatively, nucleotides can be synthesized where one or more of the elements present are replaced with a radioactive isotope, e.g., hydrogen with tritium.

Enzymes of interest as labels include hydrolases, particularly esterases and glycosidases, or oxidoreductase, particularly peroxidase. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The hybridization is usually performed by employing the probe to DNA sample affixed to a water insoluble porous support. The DNA sample is denatured so that single stranded nucleic acid is affixed. For lysing, chemical lysing is conveniently employed, usually dilute aqueous alkali, e.g., 0.1 to 1 M NaOH. The alkali can also serve to denature the DNA. Other denaturation agents include, but not limited to, elevated temperatures, organic reagents, e.g., alcohols, amides, amines, urease, phenols and sulfoxides or certain inorganic ions, e.g., thiocyanate and perchlorate.

The blood H. pylori antigens can also be detected by immunological methods which include, but not limited to, immunoblotting and immunoassays (such as basic sandwich immunoassay, triple sandwich immunoassay, and immunochromatography), using an affinity purified antibody against H. pylori. The preferred blood sample is serum.

Immunoblotting requires fractionation of blood sample using a polyacrylamide gel electrophoresis, followed by transferring the separated protein/peptide bands to a nitrocellulose membrane. The separated protein/peptide bands are then interacted with a primary antibody against *H. pylori* to form an antigen-antibody complex. A secondary antibody, which is labeled with a detection agent, against the primary antibody is then added to show the detection reaction.

Both the basic and triple sandwich immunoassays require a minimum of at least three elements: a first antibody against *H. pylori* antigen, a second antibody against *H. pylori* antigens, and a testing sample (i.e., a serum sample).

The first and second antibodies (i.e., against *H. pylori* antigen) are preferably polyclonal antibodies. This antibody can be obtained by means of injecting rabbits or other mammals, such as goats or cows, with *H. pylori* cells, preferably being disrupted by sonication, or other cell breaking means so as to present multiple antigenic sites.

In general, the antibodies are produced by an initial injection followed by subsequent booster injections to maximize the response. To produce the antibodies, the antigens are combined with adjuvants to immunize animals, such as Freunds adjuvant, to amplify the immune response. The amount of antigens injected must be adequate to elicit a sufficient amount of antibody to be detectable. Multiple injections can be made at regular intervals to optimize antibody production. The schedule of injections depend on the animal used. Animals are bled, first gauging antibody production by test bleeds. Antibody production is verified using a trial bleed and enzyme immunoassay (EIA). The antibodies are purified by chromatography, preferably, an affinity column chromatography.

In the basic sandwich assay, if the first antibody is bound to a solid carrier, the second antibody must be labeled with a detection agent, which can be any labels used in known immunometric assays. For example, enzymatic markers (such as alkaline phosphatase, horseradish peroxidase, etc.), fluorescent, luminescent or radioactive labels (such as fluorescein, rhodamine, europium, luminol, acridium and radioactive isotopes $I^{125}$, etc.), or colloidal particles (such as gold and selenium, etc.) are among the labels which can be used in the immunoassays. Among these labels, the most common one is the enzymatic markers such as horseradish peroxidase (HRP) or alkaline phosphatase. In particular, HRP label can be detected in a colorimetric assay by reacting the HRP with diamino benzidine, tetramethylbenzidine, 4-chlor-1-naphthol, or other similar chemical reaction. The colorimetric reaction product can be detected in a plate reader, scanner, densitometer or observed visually. The quantity of *H. pylori* can be determined by comparing the sample readings to those of the standards which contain a known amount of antigen. Preferably several standards are used to "bracket" the concentration of label in the test sample.

Radioisotope such as $^{125}I$ iodine or β-emitters such as $^{14}C$ carbon is another commonly used label which can be detected by gamma counters or scintillation counters. Fluorescent labels can also be used to label antibodies for detection by fluorimetry.

The solid carrier can be any solid support known to be used for immunoassays. It can be a support such as a multiwell plate for ELISA, which may be read in a plate reader. Alternatively, it can be one that allows chromatographic analysis of the sample as a liquid or solubilized in mobile phase. Examples of such a support include membranes such as nitrocellulose or media for column chromatography.

The following non-limiting examples are included to illustrate the detection of *H. pylori* antigens in blood.

EXAMPLE 1

Preparation of *H. pylori* Antigens and Nucleic Acids

*H. pylori* seed stocks of ATCC strains 43504, 43571, 43629, and 49053 were individually thawed at room temperature and diluted in 5 ml Brucella broth. Immediately after dilution, 0.2 ml of the diluted bacteria suspension were spread on a Trypticase soy blood agar plate, supplemented with 5% sheep blood. Plates were incubated under microaerobic condition for the bacteria to grow. After incubation, colonies were then scraped off the plate and washed two times with PBS. The washed pellets were then suspended in PBS.

To collect antigens from each of *H. pylori* strain, *H. pylori* cells were transferred to an iced container and subjected to sonication with a Microson XL200 ultrasonic cell disrupter for 10 minutes. The sonicated bacteria suspension was then centrifuged at 25,000×g for 30 minute at 2–8° C. The supernatant was saved for use as immunogen for producing *H. pylori* antibody.

To collect nucleic acids from each of *H. pylori* strain, *H. pylori* cells can be lysed using 1% SDS in 100 mM Tris-HCl (pH 8.8). The lysate can then be extracted once with an equal volume of phenol/chloroform, followed by twice extractions with an equal volume of phenol/chloroform/isoamyl alcohol (25:24:1). After the chloroform-phenol extractions, the chromosomal DNA can be precipitated with 0.6 volumes of isopropanol at room temperature. After centrifugation at 13,000×g for 15 minutes, the nucleic acid pellet can be washed with 70% ethanol and dissolved in 10 mM Tris-HCl and 1 mM EDTA, pH 8.0.

EXAMPLE 2

Detection of *H. pylori* DNA in Blood Using PCR Amplification

The DNA obtained from *H. pylori* strains can be digested with restriction endonucleases. Suitable restriction endonucleases include, but not limited to, HindIII, EcoRI, BamHI, ClaI, and XbaI. The resulting fragments can be electrophoresed on an agarose gel in a Tris-acetate-EDTA buffer. The DNA fragments can be extracted from the agarose gel with an agarose gel extraction kit purchased from Boehringer Mannheim (Germany). Because *H. pylori* strains are highly diverse at a genetic level, it is beneficial to compare the DNA fragments from each of the *H. pylori* strain to find consensus fragments.

The DNA sequence of the consensus fragment can be determined on both strands using double-stranded DNA templates and the dideoxy chain termination procedure as described by Sanger et al., *Proc. Natl. Acad. Sci. USA* (1977), 71:1342–1346. Based on the conserved sequence of the consensus fragments, oligonucleotide primers can be synthesized using a DNA synthesizer by following the manufacturer's protocol. Primers for PCR are usually about 20 bp in length and the preferable range is from 15–25 bp. Better amplification can be obtained when both primers are the same length and with roughly the same nucleotide composition. PCR primers which hybridize only with nucleic acids specific for the antigen are preferred, because the presence of amplification indicates the presence of the *H. pylori* specific nucleotide sequences.

DNA encoding antigenic fragments can be obtained by the skilled artisan using routine methods and a routine amount of experimentation following the procedures for obtaining the exemplary nucleic acids.

PCR amplification can be performed in a reaction mixture containing plasma DNA extract as template, *H. pylori* antigen primers, Dynazyme buffer (which can be purchased from Finnzymes, Espoo, Finland), a mixture of all four deoxynucleotides, and Dynazyme. The plasma DNA is extracted by the same way as the nucleic acid extraction for *H. pylori* cells, except that an additional step of passing the extract through a Microcon 100 filter is added to the end. This final step is to remove remaining nonbiological inhibitory substances as well as complex polysaccharides, which have been found to be potent PCR inhibitors, and allows elimination of DNA precipitation.

The reactions can be overlaid with mineral oil and heated to 94° C. for 10 minutes before the start of the PCR cycle in a Perkin-Elmer DNA Thermal Cycler (Norwalk, Conn., USA). The first 5 cycling parameters can be: denaturing for 2 minutes at 94° C., annealing for 1 minute at 42° C., and extension for 1 minute at 72° C. This can be followed by 30-cycle PCR using the following parameters: denaturing for 2 minutes at 94° C., annealing for 1 minute at 59° C., and extension for 1 minute at 72° C. During the final cycle, extension can be for 10 minutes. PCR reactions can be stopped at 4° C., and the PCR products can be analyzed on an agarose gel. The size of the PCR products can be estimated and compared to the consensus fragments found in *H. pylori* strains.

A size that is equal to the size of the consensus fragment is considered a positive result. The PCR product can be confirmed to be *H. pylori* sequence by Southern blot hybridization with $^{32}$P CTP labeled DNA probe that has been amplified from the consensus fragment. Alternatively, the PCR product and the consensus fragment can be digested with restriction enzymes such as AluI, HinfI and HaeIII, and the digests can be analyzed for digestion patterns by agarose gel electrophoresis. An identical pattern indicates that the PCR product is derived from the *H. pylori* sequences.

EXAMPLE 3

Detection of *H. pylori* DNA in Blood Using LCR Amplification

A ligase chain reaction (LCR) assay requires two sets of two oligonucleotides and a DNA ligase. The first set of oligonucleotides (i.e., Oligo A and Oligo B) are continuous to each other and complementary to one strand of the target DNA duplex. The second set of oligonucleotides (i.e., Oligo C and Oligo D) are complementary to the first set, and therefore occupy adjacent sites on the second strand of the target DNA. All four oligonucleotide probes can be designed according to the conserved sequence of the *H. pylori* strains and synthesized on an Applied Biosystems (Foster City, Calif.) oligonucleotide synthesizer and purified by PAGE. Oligo A and Oligo D can be radiolabeled at their 5' ends by incubating for 30 minutes at 37° C. in the presence of adenosine 5' ($\gamma$-$^{32}$P) triphosphate and polynucleotide kinase in 50 mM Tris-HCl (pH 7.5), 7 mM $MgCl_2$, and 1 mM dithiothreitol. The polynucleotide kinase can then be inactivated by heating at 70° C. Equal amounts of each of the radiolabeled oligonucleotides probes A and D, and each of the oligonucleotides probes B and C can be added to an eppendorf tube, along with the DNA template extracted from the serum sample. Each tube contains a reaction buffer, consisting of 50 mM bis-Tris pH 6.5, 10 mM $MgCl_2$, 10 mM $NH_4Cl$, 10 mM KCl, 1 mM dithiothreitol and 1 mM NAD. Then, an adequate amount of mineral oil can be overpaid into each tube, and the tubes can be heated to 100° C. for 3 minutes, followed by cooled to 85° C. for 1 minute, and kept at 55° C., while DNA ligase is added. The preferred DNA ligase is Pfu DNA ligase which is derived from *Pyrococcus furiosus*. The reaction tubes can then be placed in a DNA thermocycler (RoboCycler, Stratagene) and cycled between 85° C. and 50° C. 20, 30, or 40 times, for 1 minute at each temperature. An aliquot of each reaction can then be diluted 1:1 with 95% formamide stop dye. This diluted sample can be analyzed on an acrylamide gel.

EXAMPLE 4

Preparation of *H. pylori* DNA Probes

The *H. pylori* DNA fragment (normally has at least 25 bases, more usually at least about 30 bases, and may have up to about 10,000 bases or more, but usually has no more than about 5,000 bases) from *H. pylori* strains can be cut off and extracted from agarose gel after electrophoresis. This DNA fragment can be digested with a restriction endonuclease and ligated with a vector to form a recombinant plasmid construct. For example, the DNA fragment can be digested with ClaI and ligated into a ClaI-digested Pev-Vrf expression vector (Crowl et al., *Gene* (1985), 38:31–38). The recombinant plasmid can then transform a host cell which can be a prokaryotic cell such as *E. coli* RRI, or a eukaryotic cell such as NIH 3T3 cells or HeLa cells. The recombinant plasmids can be propagated through replications in the host cells. The propagated recombinant plasmids can be isolated according to So et al., *Infect. Immun.* (1978), 21:405–411. The DNA fragment from *H. pylori* can be released from the plasmids by digestion with the same restriction endonuclease. The released *H. pylori* DNA fragment can be confirmed by agarose gel or polyacrylamide electrophoresis. This propagated DNA fragment can then be labeled with radioisotope (such as $^{32}$P, $^{3}$H, $^{14}$C, or the like) or fluorescence (such as the use of digoxigenin- and biotin-labeled DNA probes coupled with fluorescence detection methods) and used as a DNA probe.

EXAMPLE 5

Preparation of Spotted Hybridization Using *H. pylori* DNA Probes

Nitrocellulose filters can be sterilized by boiling in water or autoclaved. A single sterile filter can be placed on the surface of agar and spotted with serum which has been treated to liberate its DNA. For example, the serum sample can be lysed with dilute aqueous alkali (e.g., 0.1 to 1 M NaOH). The alkali can also serve to denature the DNA. Other denaturation agents include, but not limited to, elevated temperatures, organic reagents (e.g., alcohols, amides, amines, ureas, phenols and sulfoxides) or certain inorganic ions (e.g., thiocyanate and perchlorate).

After denaturation of the sample, the filter can be washed in an aqueous buffered solution, generally at a pH of about 6 to 8, usually 7. After the lysing, denaturing and washes, the sample DNA spotted filter can be dried at an elevated temperature, generally from about 50° C. to 70° C., to fix the sample DNA on the filter.

The filter can then be incubated at a mildly elevated temperature for a sufficient time with the hybridization solution without the probe to thoroughly wet the filter. Various hybridization solutions may be employed, comprising from about 20 to 60 volume, preferably 30, percent of an inert polar organic solvent. A common hybridization solution employs about 50% formamide, about 0.5 to 1 M sodium chloride, about 0.05 to 0.1 N sodium citrate, about 0.05 to 0.2% sodium dodecylsulfate (SDS), and minor amounts of EDTA, ficoll (about 300–500 kdal), polyvinylpyrrolidone (about 250–500 kdal) and serum albumin. Also included in the hybridization solution may be from about 0.5 to 5 mg/ml of sonicated denatured DNA (e.g., calf thymus or salmon sperm), and optionally from about 0.5 to 2% wt/vol glycine. Other additives may also be included, such as dextran sulfate of from about 100 to 1,000 kdal and in an amount of from about 8 to 15 wt % of the hybridization solution.

The amount of the labeled DNA probe varies widely, depending upon the nature of the label and whether it can reasonably bind to the filter, and the stringency of the hybridization. In general, substantial excesses over stoichiometric of the probe should be employed to enhance the rate of binding of the probe to the fixed sample DNA.

After rinsing the filter at room temperature with a second solution having analogous concentrations of sodium chloride, sodium citrate and SDS as provided in the hybridization solution, the filter may now be assayed for the presence of duplexes in accordance with the nature of the label. Where the label is radioactive, the filter is dried and exposed to X-ray film. If the label is fluorescence, it can be viewed directly using a fluorescence microscope.

The probe need not have perfect complementary to the sequence to which it hybridizes; there may be 30% or more of mismatched pairs. Conditions that influence the formation of DNA hybrids are well known and described in detail by Crosa et al., *J. Bact.* (1973), 115(3):904–911.

EXAMPLE 6

Production of Rabbit Polyclonal Antibody against *H. pylori*

New Zealand white rabbits are first immunized with 0.5 to 1.0 mg of *H. pylori* antigen in Complete Freund's Adjuvant through intramuscular injection and boosted with 0.5–1.0 mg of the same antigen in Incomplete Freund's Adjuvant every four weeks. Test bleeds were taken after the third boost for analysis. Once the antibody titer reached the desired level of approximately $10^6$, production bleeding was initiated.

Each individual bleed was first diluted to $1 \times 10^6$ in PBS. One hundred (100) µl of the diluted rabbit serum was then added to *H. pylori* antigen coated wells. After incubation at room temperature for 1 hour, the plate was washed 4 times with PBS and 100 µl of goat anti-rabbit IgG-HRP conjugate was added. The plate was incubated at room temperature for an additional 30 minutes. After washing 4 times with PBS, 100 µl of tetramethylbenzidine (TMB) substrate was added to each well for color development and the color intensity in each well was measured at 450/650 nm using a microwell reader. The OD 450/650 must be greater than 1.0 to be qualify for use in antibody production.

EXAMPLE 7

Preparation of Antibody-HRP Enzyme Conjugates

Enzyme horseradish peroxidase (HRP) was selected for conjugation to anti-*H. pylori* antibody. The antibody-HRP enzyme conjugates production was based on the modified method of Nakane (Nakane et al, 1978: In immunoflorescence and related staining techniques, Knapp, et al., eds., p215–220, Elsivier/North-Holland Biomedical Press, Amsterdam).

Briefly, HRP was first subjected to an oxidation treatment with sodium m-periodate. This oxidation generates an aldehyde group on the carbohydrate side chain. The antibody and oxidized HRP were than mixed in alkaline pH, allowing the amino group on the antibody to react with the aldehyde group on HRP to form a Schieff base and reduced to a covalent bond between antibody and HRP. The antibody-HRP conjugate was then purified by gel filtration with a sephacryl-300 column.

The HRP can be conjugated to a primary antibody such as a rabbit antibody against *H. pylori,* or a secondary antibody such as a goat antibody against rabbit IgG.

EXAMPLE 8

Gel Electrophoresis and Immunoblot Analysis

Serum sample can be analyzed by SDS-PAGE. After electrophoresis, gels can be fixed and proteins can be resolved by the modified silver stain method of Oakley et al., *Anal. Biochem.* (1980), 105:361–363.

Alternatively, proteins can then be transferred to nitrocellulose paper by electro blotting for 1 hour at 1 amp. After blocking the unoccupied binding sites with a blocking agent such as TWEEN 20 and nonfat milk, a sufficient amount of *H pylori* antibody as described in Example 6 (supra) is then added to the nitrocellulose paper. The nitrocellulose paper can then be incubated at room temperature for 1 hour. Finally, alkaline-phosphatase conjugates of a secondary antibody against immunoglobulin of the animal species producing the anti-*H pylori* antibody (such as goat anti-rabbit IgG) can be added to the nitrocellulose paper. The reaction can be detected by adding 5-bromo-4-chloro-3-indolylphosphate (BCIP)/nitroblue tetrazolium (NBT).

EXAMPLE 9

Preparation of Free Form Serum *Helicobacter pylori* antigens

The serum *H. pylori* antigens may exist in both free forms and as immune complexes. The free form of *H. pylori* antigens can be readily detected by an immunoassay or any antigen detection methods. For those antigens that are imuno-complexed with *H. pylori* antibodies in serum, they can be detected only after being dissociated from the immune complexes.

The proof that the serum *H. pylori* antigens exist in both the free forms and as immune complexes, and that the free form of *H. pylori* antigens can be readily detected by the ELISA of the present invention but the immune complexes do not readily detected by the same method, is demonstrated in Table 1.

Table 1 is a serum *H. pylori* spiking study. None of the testing samples contain *H. pylori* antigens. However, despite the non-existence of *H. pylori* antigens in the serum, the serum sample might contain *H. pylori* antibodies (i.e., the "antibody positive sample"), probably due to previous infection, as opposed to the one which did not contain any *H. pylori* antibody (i.e., the "antibody negative sample"). In the spiking group, a known amount of *H. pylori* antigens ($1 \times 10^5$ bacteria/ml), either in whole bacterial cells or cell lysate, was added to both the "antibody negative" and "antibody positive" serum samples. In the "no spiking" group, no *H. pylori* antigens was added.

The results of Table 1 show that in the "antibody negative" samples, the addition of *H. pylori* antigens was reflected by the increase in the $OD_{450/650}$ readings. In contrast, the addition of *H. pylori* antigens in the "antibody positive" samples did not increase the $OD_{450/650}$ readings at the same level as in the "antibody negative" samples. One plausible explanation is that the added *H. pylori* antigens have formed immune complexes with the serum *H. pylori* antibodies which interfere with the ELISA measurement.

TABLE 1

Serum *H. pylori* Antigens Spiking Study

| Specimen | $1 \times 10^5$ bacteria/ml $OD_{450/650}$ | No Spiking $OD_{450/650}$ |
|---|---|---|
| Buffer | 3.866 | 0.077 |
| Ab negative sample 1 | 3.973 | 0.096 |
| Ab positive sample 1 | 0.336 | 0.120 |
| Ab positive sample 2 | 0.390 | 0.082 |

To dissociate the immune complexes of serum *H. pylori* antigens, the serum sample can be treated with a dissociation reagent or at a sample dissociation condition. There are five (5) major kinds of dissociation reagents which work well in dissociating the immune complexes. The first dissociation reagent is a high salt solution of NaCl, or KCl. The preferred high salt solution is 0.2 M to 1.5 M of NaCl or KCl. The most preferred high salt solution is 1.0 M of KCl.

The second dissociation reagent is a solution containing detergents such as SDS, TWEEN 20, octylglucoside, deoxycholate and TRITON X-100. These detergents can be used singly or in any combination(s). The preferred concentration of the detergent is 0.1 to 2.0% by weight and most favorably about 1% by weight.

The third dissociation reagent is a solution containing a chaotropic agent such as guanidine HCl, urea and potassium thiocyanate (KSCN). The preferred molarity for guanidine HCl is at 0.5 to 6 M, most preferably 2 M. The preferred molarity for urea is at 0.5 to 8 M, most preferably 3 M. The preferred molarity for KSCN is at 0.5 to 3 M, most preferably at 1.5 M.

The fourth dissociation reagent is a solution containing an organic solvent such as about 10% dioxane and about 40% ethylene glycol.

The fifth dissociation reagent is proteolytic or lipolytic enzyme such as protease or lipase. The preferred concentration for both protease or lipase is 1 to 10 units/ml.

The methods for optimizing the dissociation of the immune complex from serum (such as duration, temperature, pH etc.) are familiar to those of ordinary skill in the art through routine experimentation. After the completion of the dissociation, the dissociation reagent can be removed from the serum sample by conventional methods, such as dilution, filtration, column chromatography, dialysis etc.

Alternatively, the serum sample can be treated at a sample dissociation condition, which can be either a high or low pH, or an elevated temperature. The preferred high pH is 9 or higher. The preferred low pH is 3 or lower. The preferred elevated temperature is at least 50° C. The alteration of pH or temperature of the serum sample is familiar to those of ordinary skill in the art. After the completion of the alteration, the serum sample can be readjusted to the original condition by re-adjusting the pH to 7.4 or return the elevated temperature to room temperature.

Furthermore, the dissociation treated serum sample can be treated with a protein based reagent to minimize cross-reactivity. The preferred protein based reagent contains at least one of the following proteins: fetal bovine serum, pig serum, normal goat serum, horse serum, casein, albumin, gelatin, and bovine serum albumin.

EXAMPLE 10

Affinity Purification of Rabbit Anti-*H. pylori* Antibody

A. Preparation of Affinity Column

One-five (1–5) gram of *H. pylori* cell paste was suspended in 12.5 ml of PBS buffer 0.1M sodium phosphate, 0.15M NaCl, pH 7.2, containing octylglucoside and stirred at room temperature for 30 minutes. The suspension was then sonicated for 10 minutes at maximum energy output in an ice bath using 1-minute intermittence for each minute of sonication. After sonication, the insoluble materials were removed by centrifugation at 25,000 g for 30 minute. Supernatant was saved and protein concentration was adjusted to 1–3 mg/ml with PBS. Preequilibrated Aminolink coupling gels (manufactured by Pierce) in PBS were then added to the supernatant at a ratio of 1–10 mg proteins per ml of packed gels, followed by 10–40 µl of 5M sodium cyanoborohydride in water for each ml of the packed gels. The reaction slurry was then incubated at 4° C. overnight (at least 6 hours) with gentle mixing. After incubation, the gel slurry was poured into an appropriate size chromatography column and the excess liquid was drained. The column was then eluted with two column volumes of coupling buffer, followed by two column volumes of 1M Tris HCl, pH 7.4. The washed gel was resuspended in 1 column volume of the 1M Tris HCl, pH 7.4 buffer. After resuspension, 10–40 µl of 5 M sodium cyanoborohydride per ml of packed gel was added. The resulting suspension was incubated at room temperature with gentle agitation for one hour. The column was then drained, washed extensively with PBS to remove any unconjugated antigens in the column.

B. Purification of Antibody by Affinity Column

To purify the rabbit antibody, an equal volume of saturated ammonium sulfate solution was added slowly to an equal volume of rabbit serum to precipitate *H. pylori* antibodies. After stirring at room temperature for 30 minutes, the precipitates were collected by centrifugation for 30 minutes, re-dissolved in PBS and dialyzed against 100 fold excess of PBS. After dialysis, the solution was filtered through a 0.2 µm filter and loaded on to the affinity column. After loading, the column was washed extensively with PBS until eluent reached the base line. The anti-*H. pylori* specific antibody in the column was then eluted with 3M KSCN in water. Fractions containing immunoglobulins were pooled and dialyzed against PBS with minimum of two changes to remove excess KSCN. The purified antibody was then concentrated to about 1.0–2.0 mg/ml and stored at −20° C.

EXAMPLE 11

Serum Antigen ELISA Test

Serum was separated from whole blood by standard methods. The free form serum sample was collected according to Example 1. Affinity purified antibody was serially diluted in phosphate buffer between 20 µg/ml and 1.0 µg/ml. A 0.1 ml aliquot of each dilution was added to a Costar EIA Strip Plate, covered and incubated over night at room temperature. The plate was washed once with PBS and blocked with 1% BSA in PBS for 4 hours at room temperature. After BSA solution was removed, 0.1 ml of the free form serum sample was added to the antibody coated microwell strip plate, covered and incubated 2 hours at room temperature. The plate was than washed 5 times with PBS TWEEN wash. Then, 0.1 ml of rabbit anti-*H. pylori* conjugated to horseradish peroxidase was added to each microwell, covered and incubated 1 hours at room temperature. Again, the plate was washed 5 times with PBS/TWEEN wash and then developed for 10 minutes at room temperature with 0.1 ml of tetramethylbenzidine. Color development was measured at 450 nm. The reaction was stopped with 0.1 ml of 1 N H2SO$_4$. The dilution yielding the maximum optical density and lowest background was chosen as the optimal dilution.

Tables 2 and 3 represent two experiments taken at different times with different patients serum samples. These experiments show the results of the serum ELISA test for *H. pylori*. The first experiment (Table 2) includes 5 subjects. The second experiment (Table 3) includes 3 subjects. The results are expressed as OD$_{450/650}$. The presence and quantity of *H. pylori* antigens can be measured at 450 nm wavelength (650 mn represents the wavelength which detects the background [i.e., the plate]). OD$_{450/650}$ represents the reading at OD$_{450}$ subtracted by the reading at OD$_{650}$. Samples with OD$_{450/650}$ <0.1 show negative results (i.e., no *H. pylori* infection).

TABLE 2

Serum ELISA Test (Experiment 1)

|  | OD$_{450/650}$ | Result |
| --- | --- | --- |
| Pos Sample #1 | 0.712 | Positive |
| Pos Sample #2 | 0.487 | Positive |
| Pos Sample #3 | 0.187 | Positive |
| Neg Sample #4 | 0.076 | Negative |
| Neg Sample #5 | 0.048 | Negative |

TABLE 3

Serum ELISA Test (Experiment 2)

|  | OD$_{450/650}$ | Result |
| --- | --- | --- |
| Pos Sample #6 | 0.311 | Positive |
| Pos Sample #7 | 3.846 | Positive |
| Neg Sample #8 | 0.083 | Negative |
| Buffer | 0.097 | Negative |

EXAMPLE 12

Comparative Studies Between Using Affinity Purified and DEAE Purified *H. pylori* Abs in Immunoassay Table 4 shows a comparative study between using an affinity column purified *H. pylori* antibody and a DEAE column purified *H. pylori* in ELISA.

The purification of *H. pylori* antibody by affinity column is described in Example 5 (supra). The DEAE (diethylaminoethyl cellulose) column is described as follows:

A DEAE column was equilibrated with 0.0175 M potassium phosphate (pH 6.5) at room temperature. The supernatant which contained the *H. pylori* antibodies was placed over the column. The effluent fractions were collected. A protein concentration (OD$_{280}$) was determined and all fractions greater than 0.200 were pooled.

Both the affinity purified and the DEAE purified antibodies were serially diluted in phosphate buffer between 20 ug/ml and 2.0 ug/ml. A 0.1 ml aliquot of each dilution was added to a Costar EIA Strip plate, covered and incubated over night at room temperature. The plate was washed once with PBS and blocked with 1% BSA in PBS for 4 hours at room temperature. Several positive and negative specimens were diluted 1:5 in sample diluent (PBS-BSA). Each sample (0.1 ml) was added to a well of DEAE antibody coated strip or a well of affinity purified antibody-coated strip (serves as control) and incubated simultaneously with 0.1 ml of previously accepted DEAE and/or affinity purified rabbit anti-*H. pylori* horseradish enzyme conjugate (see Table 4). After 60 minutes of incubation at room temperature, the sample was thoroughly washed to remove unbound samples and enzyme labeled antibodies. Tetramethylbenzidine substrate was added and incubated for 10 minutes at room temperature. Color development was stopped with 0.1 ml of 1N sulfuric acid and wells were read at OD 450/650 mn spectro-photometrically to determine the reactivity of each sample.

TABLE 4

Comparison of DEAE and Affinity purified antibodies

|  | Assay 1 | Assay 2 | Assay 3 | Assay 4 |
| --- | --- | --- | --- | --- |
| Plate | Affinity | Affinity | DEAE | DEAE |
| Conjugate | Affinity | DEAE | DEAE | DEAE (half strength) |
| Negative Control | 0.009 | 0.223 | 0.212 | 0.085 |
| Positive Control | 1.320 | 1.366 | 1.111 | 0.879 |
| Positive Sample 1 | 2.364 | 2.813 | 1.259 | 0.766 |
| Negative Sample 2 | 0.013 | 0.154 | 0.114 | 0.049 |
| Negative Sample 3 | 0.024 | 0.323 | 0.245 | 0.112 |
| Positive Sample 4 | 0.354 | 0.398 | 0.158 | 0.084 |

Table 4 clearly show that the affinity purified antibody and affinity purified conjugate produced the best results in terms of low background reading and high (more sensitive) positive sample reading. Affinity purified antibody was used for both sides of plate and conjugate as the reference standard (Assay 1). All other assay results were compared with the reference standard. When compared with the reference standard, the DEAE plate and DEAE conjugate showed a false positive result due to the elevated background (i.e., higher OD for negative samples) and the OD of the positive samples decreased (Assay 3). By substituting the DEAE plate from the Affinity plate, the positive signals were brought up, but the higher background remained which gave false positive results (Assay 2). By lowering the DEAE conjugate concentration to 50% of original, the background was decreased but the positive signals also decreased which showed a false negative result (Assay 4).

EXAMPLE 13

Immunochromatographic Assay

An immunochromatographic assay device had an outside plastic cassette with two windows: "a sample addition window" and a "results-viewing window". The "sample addition window", to which a mobile phase was added, also contained a "label pad" or reservoir containing the second antibody, which was labeled with detection agents such as immuno-gold. The pad was placed between the sample addition spot and lower edge of the "result viewing window". The "results viewing window" was over the stationary phase, it contained a test line which was spotted with a first primary antibody and a control line which was spotted with antibody against a second primary antibody. The test line was between the sample addition window and the control line.

To perform the test, 4–6 drops of serum were added to the sample area of the cassette. The sample flowed through a label pad containing a purified *H. pylori* antibody coupled to red color of immuno-golds or other label. The sample, now containing labeled antibody, moved up the test strip which passed first the test line and then the control line. If the sample contains *H. pylori* antigens, the antibody would bind to the antigen coupled to the red immuno-golds which, in turn, would bind to a *H. Pylori* antibody spotted (immobilized) on the nitrocellulose membrane in the form of a line. As the *H. pylori* antibody-antigen-antibody complex was captured, a red test line would be visible in the result window (membrane-antibody:antigen:antibody-red immuno-gold). The control line was spotted with goat anti-rabbit antibody. *H. Pylori*-immuno-gold-antibodies were captured by goat anti-rabbit line when the sample flowed through (if a monoclonal antibody was used for coupling of colored particles, the control line should be spotted with goat anti-mouse) to assure the procedure was performed correctly.

Sample liquid, which might contain additional mobile phase, would move from lower part to the upper part (chromatographic effect) and all excess liquid would be drawn toward upper part of cassette by an absorbent pad laying at the top. If no antigen was contained in the sample, only the control line would be visible at the end of the test. If antigen was present, the test line would be visible.

Having described the invention in detail and by reference to the preferred embodiments it will be apparent to those skilled in the art that modifications and variations are possible without departing from the scope of the invention as defined in the following appended claims.

What is claimed is:

1. A method for detecting a *Helicobacter pylori* antigen in a serum sample obtained from a human comprising:
   providing said serum sample from said human; wherein said human has symptoms of peptic ulcer disease and/or chronic gastritis;
   treating said serum sample with a dissociation reagent;
   removing said dissociation reagent from said serum to form a dissociation reagent-removed serum sample;
   providing a first antibody against *Helicobacter pylori*, wherein said first antibody is a
   lyclonal antibody purified by an affinity column with potassium thiocynate (KSCN) in water;
   contacting said dissociation reagent-treated serum sample with the first antibody to form a first complex;
   providing a second antibody against *Helicobacter pylori*, wherein said second antibody is a polyclonal antibody purified by an affinity column with potassium thiocynate (KSCN) in water;
   wherein said first antibody and said second antibody are eluted from said affinity column with potassium thiocynate (KSCN) in water;
   wherein one of said first and second antibody is bound to a solid carrier, the other is labeled with a detection agent;
   contacting said first complex with the second antibody to form a second complex; and
   detecting the presence of said *Helicobacter pylori* antigen by measuring the presence of the detection agent in said second complex.

2. The method according to claim 1, wherein said solid carrier is polyethylene, polystyrene, polypropylene, or a nitrocellulose membrane.

3. The method according to claim 1, wherein said detection agent comprises at least one selected from the group consisting of an enzymatic marker, a fluorescent agent, a luminescent agent, a radioactive label, and a color particle.

4. The method according to claim 3, wherein said enzymatic marker comprises an alkaline phosphatase or horseradish peroxidase.

5. The method according to claim 3, wherein said fluorescent or luminescent agent comprises at least one selected from the group consisting of fluorescein, rhodamine, europium, luminol, and acridium.

6. The method according to claim 3, wherein said color particle comprises at least one consisting of gold, silver, blue latex, and selenium.

7. The method according to claim 3, wherein said first antibody is bound to said solid carrier and said second antibody is labelled with said enzymatic marker.

8. The method according to claim 3, wherein said first antibody is labelled with said color particle and said second antibody is bound to said solid carrier.

9. The method according to claim 1, wherein said dissociation reagent is removed from said sample by dilution, filtration, column chromatography, or dialysis.

10. The method according to claim 1, further comprising treating said dissociation reagent-removed serum sample with a protein based reagent.

11. The method according to claim 10, wherein said protein based reagent is at least one selected from the group consisting of fetal bovine serum, pig serum, goat serum, horse serum, casein, albumin, gelatin, and bovine serum albumin.

12. A method for detecting a *Helicobacter pylori* antigen in a serum sample obtained from a human comprising:
    providing said serum sample from said human; wherein said human has symptoms of peptic ulcer disease and/or chronic gastritis;
    treating said serum sample with a dissociation reagent; wherein said dissociation reagent comprises a NaCl or KCl solution at a concentration between 0.2 M to 1.5 M;
    removing said dissociation reagent;
    providing a first antibody against Helicobactur pylori, wherein said first antibody is a polyclonal antibody purified by an affinity column; contacting said dissociation reagent-treated serum sample with the first antibody to form a first complex;
    providing a second antibody against *Helicobacter pylori*, wherein said second antibody is a polyclonal antibody purified by an affinity column;
    wherein one of said first and second antibody is bound to a solid carrier, the other is labeled with a detection agent;
    contacting said first complex with the second antibody to form a second complex; and
    detecting the presence of said *Helicobacter pylori* antigen by measuring the presence of the detection agent in said second complex.

13. A method for detecting a *Helicobacter pylori* antigen in a serum sample obtained from a human comprising:
    providing said serum sample from said human; wherein said human has symptoms of peptic ulcer disease and/or chronic gastritis;
    treating said serum sample with a dissociation reagent; wherein said dissociation reagent comprises a detergent which comprises at least one selected from the group consisting of sodium dodecyl sulphate (SDS), TWEEN 20, octylglucoside deoxycholate, and TRITON X-100 at a concentration between 0.1 to 2.0% by weight;

removing said dissociation reagent:
providing a first antibody against *Helicobacter pylori*, wherein said first antibody is a polyclonal antibody purified by an affinity column:
contacting said dissociation reagent-treated serum sample with the first antibody to form a first complex;
providing a second antibody against *Helicobacter pylori* wherein said second antibody is a polyclonal antibody purified by an affinity column;
wherein one of said first and second antibody is bound to a solid carrier, the other is labeled with a detection agent;
contacting said first complex with the second antibody to form a second complex; and
detecting the presence of said *Helicobacter pylori* antigen by measuring the presence of the detection agent in said second complex.

14. A method for detecting a *Helicobacter pylori* antigen in a serum sample obtained from a human comprising:
providing said serum sample from said human; wherein said human has symptoms of peptic ulcer disease and/or chronic gastritis;
treating said serum sample with a dissociation reagent; wherein said dissociation reagent comprises an organic solvent which comprises at least one selected from the group consisting of dioxane and ethylene glycol;
removing said dissociation reagent;
providing a first antibody against *Helicobacter pylori*, wherein said first antibody is a polyclonal antibody purified by an affinity column;
contacting said dissociation reagent-treated serum sample with the first antibody to form a first complex;
providing a second antibody against *Helicobacter pylori* wherein said second antibody is a polyclonal antibody purified by an affinity column;
wherein one of said first end second antibody is bound to a solid carrier, the other is labeled with a detection agent;
contacting said first complex with the second antibody to form a second complex; and
detecting the presence of said *Helicobacter pylori*, antigen by measuring the presence of the detection agent in said second complex.

15. The method according to claim 14, wherein said dioxane is at a concentration of about 10% by weight and ethylene glycol is at a concentration of 40% by weight.

16. A method for detecting a *Helicobacter pylori* antigen in a serum sample obtained from a human comprising:
providing said serum sample from said human; wherein said human has symptoms of peptic ulcer disease and/or chronic gastritis;
treating said serum sample with a dissociation reagent; wherein said dissociation reagent comprises a chaotropic agent which is selected from the group consisting of guanidine HCl, urea, and potassium thiocyanate (KSCN);
removing said dissociation reagent;
providing a first antibody against *Helicobacter pylori*, wherein said first antibody is a polyclonal antibody purified by an affinity column;
contacting said dissociation reagent-treated serum sample with the first antibody to form a first complex;
providing a second antibody against *Helicobacter pylori*, wherein said second antibody is a polyclonal antibody purified by an affinity column;
wherein one of said first and second antibody is bound to a solid carrier, the other is labeled with a detection agent;
contacting said first complex with the second antibody to form a second complex; and
detecting the presence of said *Helicobacter pylori* antigen by measuring the presence of the detection agent in said second complex.

17. The method according to claim 16, wherein said guanidine HCl is at a molarity of 0.5 to 6 M, said urea is at molarity of 0.5 to 8 M, and said KSCN is at a molarity of 0.5 to 3 M.

18. A method for detecting a *Helicobacter pylori* antigen in a serum sample obtained from a human comprising:
providing said serum sample from said human; wherein said human has symptoms or peptic ulcer disease and/or chronic gastritis;
treating said serum sample with a dissociation reagent; wherein said dissociation reagent comprises at least one enzyme which is selected from the group consisting of protease and lipase;
removing said dissociation reagent;
providing a first antibody against *Helicobacter pylori*, wherein said first antibody is a polyclonal antibody purified by an affinity column;
contacting said dissociation reagent-treated serum sample with the first antibody to form a first complex;
providing a second antibody against *Helicobacter pylori*, wherein said second antibody is a polyclonal antibody purified by an affinity column;
wherein one of said first and second antibody is bound to a solid carrier, the other is labeled with a detection agent;
contacting said first complex with the second antibody to form a second complex; and
detecting the presence of said *Helicobacter pylori* antigen by measuring the presence of the detection agent in said second complex.

19. The method according to claim 18, wherein said protease is at least one selected from the group consisting of trypsin, chymotrypsin, pepsin, V8 protease, and subtilisin.

20. The method according to claim 18, wherein said protease is at a concentration of 1 to 10 units per ml of serum.

21. The method according to claim 18, wherein said lipase is either a lipoprotein lipase from bovine milk or lipase from *Candida rugosa*.

22. The method according to claim 21, wherein said lipase is at a concentration of 1 to 10 units per ml of serum.

23. A method for detecting a *Helicobacter pylori* antigen in a serum sample obtained from a human comprising:
providing said serum sample from said human; wherein said human has symptoms of peptic ulcer disease and/or chronic gastritis;
treating said serum sample with a dissociation reagent, wherein said dissociation reagent is (a) a NaCl or KCl solution at a concentration between 0.2 M to 1.5 M, (b) a detergent which is sodium dodecyl sulphate (SDS), TWEEN 20, octylgluoside, deoxycholate, or TRITON X-100 at a concentration between 0.1 to 2.0% by weight, (c) an organic solvent which is either dioxane or ethylene glycol, (d) a chaotropic agent which is guanidine HCl, urea, or potassium thiocyanate (KSCN), (e) an enzyme which is a protease or a lipase, or (f) any combination of (a)–(e);

removing said dissociation reagent;

providing a first antibody against *Helicobacter pylori*, wherein said first antibody is a polyclonal antibody purified by an affinity column;

contacting said dissociation reagent-treated serum sample with the first antibody to form a first complex;

providing a second antibody against *Helicobacter pylori;* wherein said second antibody is a polyclonal antibody purified by an affinity column;

wherein said first antibody and said second antibody are eluted from said affinity column;

wherein said first antibody is bound to a solid carrier;

contacting said first complex with the second antibody to form a second complex;

preparing a secondary antibody against an antibody-producing animal species for said second antibody;

labeling said secondary antibody with a detection agent to form a detection agent-labeled secondary antibody;

contacting said second complex with said detection agent-labeled secondary antibody to form a third complex; and detecting the presence of said *Helicobacter pylori* antigen by measuring the presence of the detection agent in said third complex.

24. The method according to claim 23, wherein said a detection agent comprises at least one selected from the group consisting of an enzymatic marker, a fluorescent agent, a luminescent agent, a radioactive label, and a color particle.

25. A method for detecting a *Helicobacter pylori* antigen in a serum sample obtained from a human comprising:

providing said serum sample from said human; wherein said human has symptoms of peptic ulcer disease and/or chronic gastritis;

treating said serum sample at a dissociation condition to form a dissociation condition-treated serum sample; wherein said dissociation condition is obtained by changing pH of said serum sample to alkaline or acidic pH or by elevating temperature of said serum sample;

wherein said sample dissociation condition comprises elevating said serum sample to a temperature of no less than 50° C.; and wherein upon completion of said dissociation condition, said serum pH or said elevated serum temperature is returned to original condition;

providing a first antibody against *Helicobacter pylori*, wherein said first antibody is a polyclonal antibody purified by an affinity column;

contacting said dissociation condition-treated serum sample with the first antibody to form a first complex;

providing a second antibody against *Helicobacter pylori*, wherein said second antibody is a polyclonal antibody purified by an affinity column;

wherein one of said first and second antibody is bound to a solid carrier, the other is labeled with a detection agent;

contacting said first complex with the second antibody to form a second complex; and detecting the presence of *Helicobacter pylori* in said second complex by measuring the presence of the detection agent in said second complex.

* * * * *